US012156912B2

(12) United States Patent
Gendelman et al.

(10) Patent No.: US 12,156,912 B2
(45) Date of Patent: Dec. 3, 2024

(54) METHODS AND COMPOSITIONS FOR INHIBITING DISEASES OF THE CENTRAL NERVOUS SYSTEM

(71) Applicant: Board of Regents of the University of Nebraska, Lincoln, NE (US)

(72) Inventors: Howard E. Gendelman, Omaha, NE (US); R. Lee Mosley, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 22 days.

(21) Appl. No.: 14/401,428

(22) PCT Filed: May 20, 2013

(86) PCT No.: PCT/US2013/041814
§ 371 (c)(1),
(2) Date: Nov. 14, 2014

(87) PCT Pub. No.: WO2013/173827
PCT Pub. Date: Nov. 21, 2013

(65) Prior Publication Data
US 2015/0139937 A1     May 21, 2015

Related U.S. Application Data

(60) Provisional application No. 61/649,056, filed on May 18, 2012.

(51) Int. Cl.
*A61K 39/00*     (2006.01)
*A61K 38/17*     (2006.01)
(Continued)

(52) U.S. Cl.
CPC .......... *A61K 39/39* (2013.01); *A61K 38/1709* (2013.01); *A61K 38/193* (2013.01);
(Continued)

(58) Field of Classification Search
None
See application file for complete search history.

(56) References Cited

U.S. PATENT DOCUMENTS 5,620,708 A    4/1997   Amkraut et al.
6,787,139 B1   9/2004   Schenk et al.
(Continued)

FOREIGN PATENT DOCUMENTS

| WO | WO97/14426 | * | 4/1997 | ............. A61K 38/08 |
| WO | WO2006/045037 | * | 4/2006 | |
| WO | 2007011907 | | 1/2007 | |

OTHER PUBLICATIONS

Mishizen-Eberz et al., Cleavage of alpa-Synuclein by Calpain: Potential Role in Degradation of Fibrillized and Nitrated Species of alpha-Synuclein. Biochemistry 2005, 44, 7818-7829.*
(Continued)

*Primary Examiner* — Aurora M Fontainhas
(74) *Attorney, Agent, or Firm* — Robert C. Netter, Jr.; Dann, Dorfman, Herrell & Skillman

(57) ABSTRACT

Methods and compositions for treating central nervous system diseases and disorders are disclosed. In a particular embodiment, compositions comprising a nitrated alpha synuclein peptide are provided. The composition may further comprise an adjuvant that stimulates regulatory T cells and/or at least one pharmaceutically acceptable carrier.

2 Claims, 2 Drawing Sheets

Specification includes a Sequence Listing.

(51) Int. Cl.
  A61K 38/19    (2006.01)
  A61K 38/22    (2006.01)
  A61K 39/39    (2006.01)
  C12N 15/89    (2006.01)
(52) U.S. Cl.
  CPC ...... A61K 38/2278 (2013.01); A61K 39/0005 (2013.01); A61K 2039/555 (2013.01)

(56) References Cited

U.S. PATENT DOCUMENTS

| | | | |
|---|---|---|---|
| 7,306,945 | B2 | 11/2007 | Chilcote et al. |
| 8,491,890 | B2 | 7/2013 | Gendelman et al. |
| 2003/0086938 | A1 | 5/2003 | Birk et al. |
| 2006/0015952 | A1 | 1/2006 | Filvaroff et al. |
| 2006/0259986 | A1* | 11/2006 | Chilcote ............ A01K 67/0275 800/3 |
| 2007/0212404 | A1 | 9/2007 | Kim et al. |
| 2008/0175920 | A1 | 7/2008 | Kim et al. |
| 2009/0286745 | A1* | 11/2009 | Zurdo ................. C07K 5/0815 514/10.3 |
| 2010/0028320 | A1 | 2/2010 | Gendelman et al. |

OTHER PUBLICATIONS

Aharoni, R., et al., The immunomodulator glaliramer acetate augments the expression of neurotrophic factors in brains of experimental autoimmune encephalomyelitis mice, Proc Nall Acad Sci U S A., 2005, 102 (52), 19045-50.
Alexinau, M.E., et al., Immune reactivity in a mouse model of familial ALS correlates with disease progression, Neurology, 2001, 57(7), 1282-9.
Amoura, Z., et al., The key role of nucleosomes in lupus, Arthritis Rheum., 1999, 42(5), 833-43.
Angelov, D.N., et al. Therapeutic vaccine for acute and chronic motor neuron diseases: implications for amyotrophic lateral sclerosis, Proc Nall Acad Sci U S A., 2003, 100(8), 4790-5.
Avidan, H., et al., Vaccination with autoantigen protects against aggregated bela-amyloid and glutamate toxicity by controlling microglia: effect of CD4+CD25+ T cells, Eur J Immunol, 2004, 34(12), 3434-45.
Bakalash, S., et al., T-cell-based vaccination for morphological and functional neuroprotection in a rat model of chronically elevated intraocular pressure, J Mol Med., 2005, 83(11), 904-16.
Bal-Price, A., et al., Inflammatory neurodegeneration mediated by nitric oxide from activated glia-inhibiting neuronal respiration, causing glutamate release and excitotoxicity, J Neurosci., 2001, 21(17), 6480-91.
Banerjee, R., et al., Adaptive immune neuroprotection in G93A-SOD1 amyotrophic lateral sclerosis mice, PLoS One, 2008, 3(7), e2740.
Bar-Or, A., et al., Analyses of all matrix melalloproteinase members in leukocytes emphasize monocy1es as major inflammatory mediators in multiple sclerosis, Brain, 2003, 126(Pt 12), 2738-49.
Bas, J., et al., Lymphocyte populations in Parkinson's disease and in rat models of parkinsonism, J Neuroimmunol. 2001, 113(1), 146-52.
Benner, E.J., et al., Therapeutic immunization protects dopaminergic neurons in a mouse model of Parkinson's disease, Proc Nall Acad Sci U S A., 2004, 101(25), 9435-40.
Benner. E.J., et al., Nitrated alpha-synuclein immunity accelerates degeneration of nigral dopaminergic neurons, PLoS One, 2008, 3(1), e1376.
Brochard, V., et al., Infiltration of CD4+ lymphocytes into the brain contributes to neurodegeneration in a mouse model of Parkinson disease, J Clin Invest., 2009, 119(1), 182-92.
Burkhardt, H., et al., Chicken and egg in autoimmunity and joint inflammation, Trends Immunol., 2001, 22 (6), 291-3.

Butovsky, 0., et al., Glatiramer acetate fights against Alzheimer's disease by inducing dendritic-like microglia expressing insulin-like growth factor 1, Proc Natl Acad Sci U S A., 2006, 103(31), 11784-9.
Casal, J.A., et al., Serum markers of monocyte/macrophage activation in patients with Alzheimer's disease and other types of dementia, Clin Biochem., 2003, 36(7), 553-6.
Casciola-Rosen, L., et al., Scleroderma autoantigens are uniquely fragmented by metal-catalyzed oxidation reactions: implications for pathogenesis, J Exp Med., 1997, 185(1), 71-9.
Cederbom, L., et al., CD4+CD25+ regulatory T cells down-regulate co-stimulatory molecules on antigen-presenting cells, Eur J Immunol., 2000, 30(6), 1538-43.
Chartier-Harlin, M.C., et al., Alpha-synuclein locus duplication as a cause of familial Parkinson's disease, Lancet., 2004, 364(9440), 1167-9.
Cho, B.P., et al., Microglial phagocytosis of dopamine neurons at early phases of apoptosis, Cell Mol Neurobiol., 2003, 23(4-5), 551-60.
Choi, D.K., et al., Ablation of the inflammatory enzyme myeloperoxidase mitigates features of Parkinson's disease in mice, J Neurosci., 2005, 25(28), 6594-600.
Birnboim, H.C., et al., Cutting edge: MHC class II-restricted peptides containing the inflammation-associated marker 3-nitrotyrosine evade central tolerance and elicit a robust cell-mediated immune response, J Immunol., 2003, 171(2), 528-32.
Croisier. E., et al., Microglial inflammation in the parkinsonian subslantia nigra: relationship to alpha-synuclein deposition, J Neuroinflammation, 2005, 2, 14.
Curiel, T.J., et al., Specific recruitment of regulatory T cells in ovarian carcinoma fosters immune privilege and predicts reduced survival, Nat Med., 2004, 10(9), 942-9.
Delgado, M., et al., Vasoactive intestinal peptide generates CD4+CD25+ regulatory T cells in vivo, J Leukoc Biol., 2005, 78(6), 1327-38.
Doyle, Ha, et al., Post-translational protein modifications in antigen recognition and autoimmunity, Trends Immunol., 2001, 22(8), 443-9.
Du, Y., et al., Minocycline prevents nigrostrialal dopaminergic neurodegeneration in the MPTP model of Parkinson's disease, Proc Nall Acad Sci U S A., 2001, 98(25), 14669-74.
Dufty, B.M., et al., Calpain-cleavage of alpha-synuclein: connecting proteoly1ic processing to disease-linked aggregation, Am J Pathol., 2007, 170(5), 1725-38.
Eggena, M.P., et al., Depletion of regulatory T cells in HIV infection is associated with immune activation, J Immunol., 2005, 174(7), 4407-14.
El-Agnaf, O.M., et al., Alpha-synuclein implicated in Parkinson's disease is present in extracellular biological ftuids, including human plasma, FASEB J., 2003, 17(13), 1945-7.
Eliezer, D., et al., Conformational properties of alpha-synuclein in its free and lipid-associated states, J Mol Biol., 2001, 307(4), 1061-73.
Filion, Lg., et al., Monocyte-derived cy1okines in multiple sclerosis, Clin Exp Immunol., 2003, 131(2), 324-34.
Garg, S.K., et al., Neuroprotective immunity: T cell-derived glutamate endows astrocytes with a neuroprotective phenotype, J Immunol., 2008, 180(6), 3866-73.
Gendelman, H.E., et al., Neural immunity: Friend or foe? J Neurovirol., 2002, 8(6), 474-9.
Giasson, B.I., et al., Oxidative damage linked to neurodegeneration by selective alpha-synuclein nitration in synucleinopathy lesions, Science, 2000, 290(5493), 985-9.
Goedert, M., Filamentous nerve cell inclusions in neurodegenerative diseases: tauopathies and alpha- synucleinopathies, Philos Trans R Soc Lond B Biol Sci., 1999, 354(1386), 1101-18.
Gonzalez-Rey, E., et al., Vasoactive intestinal peptide generates human tolerogenic dendritic cells that induce CD4 and CD8 regulatory T cells, Blood, 2006, 107(9), 3632-8.
Gorantla, S., et al., Modulation of innate immunity by copolymer-1 leads to neuroprotection in murine HIV-1 encephalitis, Glia, 2008, 56(2), 223-32.

(56) References Cited

OTHER PUBLICATIONS

Graves, M.C., et al., Inflammation in amyotrophic lateral sclerosis spinal cord and brain is mediated by activated macrophages, mast cells and T cells, Amyotroph Lateral Seier Other Motor Neuron Disord., 2004, 5(4), 213-9.
Habisch, H.J., et al., Limited effects of glaliramer acetate in the high-copy No. hSOD1-G93A mouse model of ALS. Exp Neurol., 2007, 206(2), 288-95.
Haenggeli, C., et al., Therapeutic immunization with a glaliramer acetate derivative does not alter survival in G93A and G37R SOD1 mouse models of familial ALS, Neurobiol Dis., 2007, 26(1), 146-52.
Hasegawa, M., et al., Phosphorylaled alpha-synuclein is ubiquitinaled in alpha-synucleinopathy lesions, J Biol Chem., 2002, 277(50), 49071-6.
Henkel, J.S., et al., Presence of dendritic cells, MCP-1, and activated microglia/macrophages in amyotrophic lateral sclerosis spinal cord tissue, Ann Neurol., 2004, 55(2), 221-35.
Henkel, J.S., et al., The chemokine MCP-1 and the dendritic and myeloid cells iiattracts are increased in the mSOD1 mouse model of ALS, Mol Cell Neurosci., 2006, 31(3), 427-37.
Hermanowicz, N., Drug therapy for Parkinson's disease, Semin Neurol., 2007, 7(2), 97-105.
Hodara, R., et al., Functional consequences of alpha-synuclein tyrosine nitration: diminished binding to lipid vesicles and increased fibril formation, J Biol Chem., 2004, 279(46), 47746-53.
Jin, J., et al., Prostaglandin E2 receptor subtype 2 (EP2) regulates microglial activation and associated neurotoxicity induced by aggregated alpha-synuclein, J Neuroinflammation, 2007, 4, 2.
Kakimura, J., et al., Release and aggregation of cytochrome c and alpha-synuclein are inhibited by the antiparkinsonian drugs, talipexole and pramipexole, Eur J Pharmacol., 2001, 417(1-2), 59-67.
Kinter, Al, et al., CD25(+)CD4(+) regulatory T cells from the peripheral blood of asymptomatic HIV-infected individuals regulate CD4(+) and CD8(+) HIV-specific T cell immune responses in vitro and are associated with favorable clinical markers of disease status, J Exp Med., 2004, 200(3), 331-43.
Kipnis, J., et al., T cell immunity to copolymer 1 confers neuroprotection on the damaged optic nerve: possible therapy for optic neuropathies, Proc Natl Acad Sci U S A., 2000, 97(13), 7446-51.
Danielson et al., Preferentially increased nitration of alpha-synuclein at tyrosine-39 in a cellular oxidative model of Parkinson's disease, Anal. Chem, 2009, 7823-7828, 81(18).
Kipnis. J.. et al. Myelin specific Th1 cells are necessary for post-traumatic protective autoimmunity, J Neuroimmunol. 2002, 78-85, 130(1-2).
Klegeris. A., et al. Therapeutic approaches to inflammation in neurodegenerative disease, Curr Opin Neurol, 2007, 351-7, 20(3).
Kohutnicka, M., et al. Microglial and astrocylic involvement in a murine model of Parkinson's disease induced by 1-methyl-4-phenyl-1,2,3,6-tetrahydropyridine (MPTP), Immunopharmacology, 1998, 167-80, 39(3).
Krishnan, S., et al. Oxidative dimer formation is the critical rate-limiting step for Parkinson's disease alpha-synuclein fibrillogenesis, Biochemistry, 2003, 42(3), 829-37.
Kruger, R., et al., Ala30Pro mutation in the gene encoding alpha-synuclein in Parkinson's disease, Nat Genet., 1998 18(2), 106-8.
Kurkowska-Jastrzebska, I., et al., Dexamethasone protects against dopaminergic neurons damage in a mouse model of Parkinson's disease, Int. Immunopharmacol., 2004, 4(10-11), 1307-1318.
Laurie, C., et al., CD4+ T cells from Copolymer-1 immunized mice protect dopaminergic neurons in the 1-methyl-4-phenyl-1,2,3,6-tetrahydropyridine model of Parkinson's disease, J Neuroimmunol., 2007, 183(1-2), 60-8.
Lee, H.J., et al. "Intravesicular localization and exocylosis of alpha-synuclein and its aggregates." J Neurosci. 2005, 25(25), 6016-24.
Lee, H.J., et al., Clearance and deposition of extracellular alpha-synuclein aggregates in microglia, Biochem Biophys Res Commun, 2008, 372(3), 423-8.

Hodaie, M., et al., The dopaminergic nigrostriatal system and Parkinson's disease: molecular events in development, disease, and cell death, and new therapeutic strategies, Neurosurgery, 2007, 60(1), 17-28.
Ling, Z., et al., Rotenone potentiates dopamine neuron loss in animals exposed to lipopolysaccharide prenatally, Exp Neurol., 2004, 190(2), 373-83.
Lipton. SA, et al., Inflammatory mediators leading to protein misfolding and uncompetitive/fast off-rate drug therapy for neurodegenerative disorders, Int Rev Neurobiol., 2007, 82:1-27.
Liu, B., et al., Role of microglia in inflammation-mediated neurodegenerative diseases: mechanisms and strategies for therapeutic intervention, J Pharmacol Exp Ther., 2003, 304(1 ):1-7.
Liu, J., et al., T cell independent mechanism for copolymer-1-induced neuroprotection, Eur J Immunol., 2007, 37 (11), 3143-54.
Liu, J., et al. Identification of proteins involved in microglial endocytosis of alpha-synuclein, J Proteome Res., 2007, 6 (9), 3614-27.
Luo, C., et al., Alpha-synuclein and tyrosine hydroxylase expression in acute rotenone toxicity, Int J Mol Med., 2007, 19(3), 517-21.
Masliah, E., et al., Effects of alpha-synuclein immunization in a mouse model of Parkinson's disease, Neuron, 2005 46(6), 857-68.
Mcgeer, P.L., et al. Inflammation and neurodegeneration in Parkinson's disease, Parkinsonism Reial Disord., Suppl 1:S3-7.
Mevorach, D., et al., Systemic exposure to irradiated apoptotic cells induces autoanlibody production, J Exp Med. 1998, 188(2), 387-92.
Ohmori, H., et al., Immunogenicity of an inflammation-associaled product, tyrosine nitrated self-proteins, Autoimmun Rev., 2005, 224-9.
Oswald-Richter, K., et al., HIV infection of naturally occurring and genetically reprogrammed human regulatory T-cells, PLoS Biol. 2004, 2(7), E198.
Paxinou, E., et al., Induction of alpha-synuclein aggregation by intracellular nitrative insult, J Neurosci., 2001, 20, 8053-61.
Polymeropoulos, M.H. et al., Mutation in the alpha-synuclein gene identified in families with Parkinson's disease, Science, 1997, 276(5321), 2045-7.
Reynolds, A., et al., Oxidative stress and the pathogenesis of neurodegenerative disorders, Int Rev Neurobiol., 2007, 82, 297-325.
Reynolds, A.O., et al., Neuroprotective activities of CD4+CD25+ regulatory T cells in an animal model of Parkinson's disease, J Leukoc Biol., 2007, 82(5), 1083-94.
Reynolds, A.O., et al., Nitrated alpha-synuclein-activated microglial profiling for Parkinson's disease, J Neurochem., 2008, 104(6), 1504-25.
Reynolds, A.O., et al., Nitrated alpha-synuclein and microglial neuroregulatory activities, J Neuroimmune Pharmacol., 2008, 3(2), 59-74.
Reynolds, A.O., et al., Nitrated {alpha}-synuclein-induced alterations in microglial immunity are regulated by CD4+ cell subsets, J Immunol., 2009, 182(7), 4137-49.
Sakaguchi, S., Naturally arising CD4+ regulatory t cells for immunologic self-tolerance and negative control of immune responses, Annu Rev Immunol., 2004, 22, 531-62.
Scali, C., et al., Neutrophils CD11b and fibroblasts PGE(2) are elevated in Alzheimer's disease, Neurobiol Aging, 2002, 23(4), 523-30.
Schori, H., et al., T-cell-based immunity counteracts the potential toxicity of glutamate in the central nervous system, J Neuroimmunol., 2001, 119(2), 199-204.
Sidhu, A., et al., Does alpha-synuclein modulate dopaminergic synaptic content and tone at the synapse? FASEB J., 2004, 18(6), 637-47.
Singleton, A.B., et al., alpha-Synuclein locus triplication causes Parkinson's disease, Science, 2003, 302 (5646), 841.
Smith, MA, et al., Predicting the failure of amyloid-beta vaccine, Lancet, 2002, 359(9320), 1864-5.
Souza, J.M., et al., Dityrosine cross-linking promotes formation of stable alpha-synuclein polymers. Implication of nitrative and oxidative stress in the pathogenesis of neurodegenerative synucleinopathies, J Biol Chem., 2000, 275 (24), 18344-9.

(56) References Cited

OTHER PUBLICATIONS

Spillantini, M.G., et al., Alpha-synuclein in Lewy bodies, Nature, 1997, 388(6645), 839-40.
Spira, P.J., et al., Clinical and pathological features of a Parkinsonian syndrome in a family with an Ala53Thr alpha-synuclein mutation, Ann Neurol., 2001, 49(3), 313-9.
Sugama, S., et al., Age-related microglial activation in 1-methyl-4-phenyl-1,2,3,6-tetrahydropyridine (MPTP)-induced dopaminergic neurodegeneration in C57BL/6 mice, Brain Res., 2003, 964(2), 288-94.
Teismann, P., et al., Inhibition of the cyclooxygenase isoenzymes COX-1 and COX-2 provide neuroprotection in the MPTP-mouse model of Parkinson's disease, Synapse, 2001, 39(2), 167-74.
Teismann, P., et al., Cyclooxygenase-2 is instrumental in Parkinson's disease neurodegeneration, Proc Natl Acad Sci U S A., 2003, 100(9), 5473-8.
Theodore, S., et al., Targeted overexpression of human alpha-synuclein triggers microglial activation and an adaptive immune response in a mouse model of Parkinson disease, J Neuropathol Exp Neurol., 2008, 67 (12), 1149-58.
Thomas, M.P., et al., Ion channel blockade attenuates aggregated alpha synuclein induction of microglial reactive oxygen species: relevance for the pathogenesis of Parkinson's disease, J Neurochem., 2007, 100(2), 503-19.
Thornton, A.M., et al., Suppressor effector function of CD4+CD25+ immunoregulatory T cells is antigen nonspecific, J Immunol., 2000, 164(1), 183-90.
Tiemessen, M.M., et al., CD4+CD25+Foxp3+ regulatory T cells induce alternative activation of human monocyles/macrophages, Proc Natl Acad Sci U S A., 2007, 104(49), 19446-51.
Utz. P.J., et al., Posttranslational protein modifications, apoptosis, and the bypass of tolerance to autoantigens, Arthritis Rheum., 1998, 41(7), 1152-60.
Uversky, V.N., et al., Why are "natively unfolded" proteins unstructured under physiologic conditions? Proteins, 2000 41(3), 415-27.
Uversky, V.N., et al., Evidence for a partially folded intermediate in alpha-synuclein fibril formation, J Biol Chem., 2001, 276(14), 10737-44.
Uversky, V.N., et al., Effects of nitration on the structure and aggregation of alpha-synuclein, Brain Res Mol Brain Res., 2005, 134(1), 84-102.
Vijitruth, R., et al., Cyclooxygenase-2 mediates microglial activation and secondary dopaminergic cell death in the mouse MPTP model of Parkinson's disease, J Neuroinflammation., 2006, 3, 6.
Wang, HY., et al., Tumor-specific human CD4+ regulatory T cells and their ligands: implications for immunotherapy, Immunity, 2004, 20(1), 107-18.
Weinreb, P.H., et al., NACP, a protein implicated in Alzheimer's disease and learning, is natively unfolded, Biochemistry, 1996, 35(43), 13709-15.
Wersinger, C., et al., An inflammatory pathomechanism for Parkinson's disease? Curr Med Chem., 2006, 13 (5), 591-602.
Wu, D.C., et al., Blockade of microglial activation is neuroprotective in the 1-methyl-4-phenyl-1,2,3,6-tetrahydropyridine mouse model of Parkinson disease, J Neurosci., 2002, 22(5), 1763-71.
Yamin, G., et al., Nitration inhibits fibrillation of human alpha-synuclein in vitro by formation of soluble oligomers, FEBS Lett., 2003, 542(1-3), 147-52.
Zarranz, J.J., et al., The new mutation, E46K, of alpha-synuclein causes Parkinson and Lewy body dementia, Ann Neurol., 2004, 55(2), 164-73.
Zhang, W., et al., Aggregated alpha-synuclein activates microglia: a process leading to disease progression in Parkinson's disease, FASEB J., 2005, 19(6), 533-42.
Zhang, R., et al., Evidence for systemic immune system alterations in sporadic amyotrophic lateral sclerosis (sALS), J Neuroimmunol., 2005, 159(1-2), 215-24.
Zhang, R., et al., MCP-1 chemokine receptor CCR2 is decreased on circulating monocyles in sporadic amyotrophic lateral sclerosis (sALS), J Neuroimmunol., 2006, 179(10-11), 87-93.
Zhao, W., et al. Protective effects of an anti-inflammatory cytokine, interleukin-4, on motoneuron toxicity induced by activated microglia, J Neurochem., 2006, 99(4), 1176-87.
Delgado, M., et al., Vasoactive intestinal peptide and pituitary adenylate cyclase-activating polypeptide stimulate the induction of Th2 responses by up-regulating B7.2 expression, J Immunol., 1999, 163(7), 3629-35.
Delgado, M., et al., Vasoactive intestinal peptide and pituitary adenylate cyclase-activating polypeptide inhibit interleukin-12 transcription by regulating nuclear factor kappaB and Els activation, J Biol Chem., 1999, 274 (45), 31930-40.
Delgado, M., et al., Neuroprotective effect of vasoactive intestinal peptide (VIP) in a mouse model of Parkinson's disease by blocking microglial activation, FASEB J., 2003, 17(8), 944-6.
Delgado, M., et al., Vasoactive intestinal peptide and pituitary adenylate cyclase-activating polypeptide promote in vivo generation of memory Th2 cells, FASEB J., 2002, 16(13), 1844-6.
Delgado, M., et al., Vasoactive intestinal peptide prevents activated microglia-induced neurodegeneration under inflammatory conditions: potential therapeutic role in brain trauma, FASEB J., 2003, 17(13), 1922-4.
Ischiropoulos, H., et al., Oxidative stress and nitration in neurodegeneration: cause, effect, or association? J Clin Invest., 2003, 111(2), 163-9.
Wang et al., Tumor-specific CD4+ regulatory T cells and their ligands: implications for immunotherapy, Immunity, 2004, 20(1), 107-118.
Benner et al., Nitrated alpha-Synuclein immunity accelerates degeneration of nigral dopaminergic neurons, PlosOne, 2008, 3(1), 1-20.
Anderson, J.K., Oxidative stress in neurodegeneration: Cause or Consequence? Nature Reviews Neuroscience, 2004, 5, 818-825.
Zhu, M., et al., The association of alpha-synuclein with membranes affects bilayer structure, stability, and fibril formation, J Biol Chem., 2003, 278(41), 40186-97.
Chung, CY., et al., Cell type-specific gene expression of midbrain dopaminergic neurons reveals molecules involved in their vulnerability and protection, Hum Mol Genet., 2005, 14(13), 1709-25.
Zidek et al., Role of cytokines in the modulation of nitric oxide production by cyclic AMP, Eur. Cytokine Netw., 2001, 12(1), 22-32.
Sigma, Granulocyte-Macrophage Colony-Stimulating Factor (GM-CSF), Sigma Cell Culture Catalogue, 1995, p. 61.
Sigma, Vasoactive Intestinal Peptide (VIP), Sigma Peptides and Amino Acids Catalogue, 1995, p. 31.
Campbell, Inflammation, neurodegenerative diseases, and environmental exposures, Ann. NY Acad. Sci., 2004, 1035, 117-32.
Cao et al., Activated Immune Cells in Parkinson's Disease, J. Neuroimmune Pharmacol., 2011, 323-9.
Danielson et al., Preferentially Increased Nitration of alpha-Synuclein at Tyrosine-39 in a Cellular Oxidative Model of Parkinson's Disease, Anal. Chem., 2009, 81, 7823-7828.

* cited by examiner

```
  1 MDVFMKGLSK AKEGVVAAAE KTKQGVAEAA GKTKEGVLYV GSKTKEGVVH
 51 GVATVAEKTK EQVTNVGGAV VTGVTAVAQK TVEGAGSIAA ATGFVKKDQL
101 GKNEEGAPQE GILEDMPVDP DNEAYEMPSE EGYQDYEPEA
```

Figure 2

SEQUENCE LISTING

```
<160> NUMBER OF SEQ ID NOS: 13

<210> SEQ ID NO 1
<211> LENGTH: 15
<212> TYPE: PRT
<213> ORGANISM: Mus musculus

<400> SEQUENCE: 1

Lys Lys Asp Gln Met Gly Lys Gly Glu Glu Gly Tyr Pro Gln Glu
1               5                   10                  15

<210> SEQ ID NO 2
<211> LENGTH: 15
<212> TYPE: PRT
<213> ORGANISM: Mus musculus

<400> SEQUENCE: 2

Gly Lys Gly Glu Glu Gly Tyr Pro Gln Glu Gly Ile Leu Glu Asp
1               5                   10                  15

<210> SEQ ID NO 3
<211> LENGTH: 15
<212> TYPE: PRT
<213> ORGANISM: Mus musculus

<400> SEQUENCE: 3

Gly Tyr Pro Gln Glu Gly Ile Leu Glu Asp Met Pro Val Asp Pro
1               5                   10                  15
```

<210> SEQ ID NO 4
<211> LENGTH: 15
<212> TYPE: PRT
<213> ORGANISM: Mus musculus

<400> SEQUENCE: 4

```
Gly Ile Leu Glu Asp Met Pro Val Asp Pro Gly Ser Glu Ala Tyr
1               5                   10                  15
```

<210> SEQ ID NO 5
<211> LENGTH: 15
<212> TYPE: PRT
<213> ORGANISM: Mus musculus

<400> SEQUENCE: 5

```
Met Pro Val Asp Pro Gly Ser Glu Ala Tyr Glu Met Pro Ser Glu
1               5                   10                  15
```

<210> SEQ ID NO 6
<211> LENGTH: 15
<212> TYPE: PRT
<213> ORGANISM: Mus musculus

<400> SEQUENCE: 6

```
Gly Ser Glu Ala Tyr Glu Met Pro Ser Glu Glu Gly Tyr Gln Asp
1               5                   10                  15
```

<210> SEQ ID NO 7
<211> LENGTH: 15
<212> TYPE: PRT
<213> ORGANISM: Mus musculus

<400> SEQUENCE: 7

```
Glu Met Pro Ser Glu Glu Gly Tyr Gln Asp Tyr Glu Pro Glu Ala
1               5                   10                  15
```

<210> SEQ ID NO 8
<211> LENGTH: 140
<212> TYPE: PRT
<213> ORGANISM: Homo sapiens

<400> SEQUENCE: 8

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
        130                 135                 140
```

```
<210> SEQ ID NO 9
<211> LENGTH: 25
<212> TYPE: PRT
<213> ORGANISM: Homo sapiens

<400> SEQUENCE: 9

Gly Ala Pro Gln Glu Gly Ile Leu Glu Asp Met Pro Val Asp Pro Asp
1               5                   10                  15

Asn Glu Ala Tyr Glu Met Pro Ser Glu
            20                  25

<210> SEQ ID NO 10
<211> LENGTH: 15
<212> TYPE: PRT
<213> ORGANISM: Homo sapiens

<400> SEQUENCE: 10

Gly Ala Pro Gln Glu Gly Ile Leu Glu Asp Met Pro Val Asp Pro
1               5                   10                  15

<210> SEQ ID NO 11
<211> LENGTH: 15
<212> TYPE: PRT
<213> ORGANISM: Homo sapiens

<400> SEQUENCE: 11

Gly Ile Leu Glu Asp Met Pro Val Asp Pro Asp Asn Glu Ala Tyr
1               5                   10                  15

<210> SEQ ID NO 12
<211> LENGTH: 15
<212> TYPE: PRT
<213> ORGANISM: Homo sapiens

<400> SEQUENCE: 12

Met Pro Val Asp Pro Asp Asn Glu Ala Tyr Glu Met Pro Ser Glu
1               5                   10                  15

<210> SEQ ID NO 13
<211> LENGTH: 15
<212> TYPE: PRT
<213> ORGANISM: Homo sapiens

<400> SEQUENCE: 13

Asp Asn Glu Ala Tyr Glu Met Pro Ser Glu Glu Gly Tyr Gln Asp
1               5                   10                  15
```

METHODS AND COMPOSITIONS FOR INHIBITING DISEASES OF THE CENTRAL NERVOUS SYSTEM

This application is a § 371 application of PCT/US2013/041814, filed May 20, 2013, which claims priority under 35 U.S.C. § 119 (e) to U.S. Provisional Patent Application No. 61/649,056, filed on May 18, 2012. The foregoing applications are incorporated by reference herein.

This invention was made with government support under 5R01 NS070190-02 awarded by the National Institutes of Health. The government has certain rights in the invention.

FIELD OF THE INVENTION

The present invention relates to the fields of central nervous system disorders. More specifically, the invention provides compositions and methods for the treatment of central nervous disorders, particularly Parkinson's Disease.

BACKGROUND OF THE INVENTION

Several publications and patent documents are cited throughout the specification in order to describe the state of the art to which this invention pertains. Each of these citations is incorporated herein by reference as though set forth in full.

Parkinson's disease (PD) is a common progressive neurodegenerative disease clinically characterized by resting tremor, muscle rigidity, bradykinesia, and postural instability (Dauer et al. (2003) Neuron 39:889-909). PD is sporadic and of unknown cause although host genetics, environmental cues, aging, impaired energy metabolism and oxidative stress are linked to disease onset and progression (Klockgether, T. (2004) Cell Tissue Res., 318:115-120). Pathologically, PD is characterized by degeneration of dopaminergic cell bodies in the substantia nigra pars compacta (SNpc) and their associated caudate projections (Dauer et al. (2003) Neuron 39:889-909). Nonetheless, the pathological hallmark of PD is cytoplasmic inclusions of fibrillar, misfolded proteins called Lewy bodies composed principally of α-synuclein (α-Syn) (Spillantini et al. (1997) Nature, 388:839-840).

α-Syn is a 140-amino acid (aa), natively unfolded, soluble protein that is localized in the pre-synaptic terminals of neurons of the central nervous system (CNS), where it interacts with and may regulate synaptic vesicles (Spillantini et al. (1997) Nature 388: 839-840; Sidhu et al. (2004) FASEB J., 18:637-647; Paxinou et al. (2001) J. Neurosci., 21:8053-8061; Weinreb et al. (1996) Biochemistry 35:13709-13715; Eliezer et al. (2001) J. Mol. Biol., 307:1061-1073; Uversky et al. (2000) Proteins 41:415-427). Three missense mutations (A53T, A30P and E46K) in the gene encoding α-Syn are linked to dominantly inherited PD (Kruger et al. (1998) Nat. Genet., 18:106-108; Polymeropoulos, et al. (1997) Science, 276:2045-2047; Zarranz et al. (2004) Ann. Neurol., 55:164-173). Moreover, multiplication of the wild-type (WT) gene has also been linked to PD, suggesting that the level of α-Syn is an important pathogenic factor (Chartier-Harlin et al. (2004) Lancet 364:1167-1169; Singleton et al. (2003) Science 302:841). Such familial cases are rare and in sporadic PD, there is no genetic aberration of α-Syn. However, it has been proposed that post-translational modifications such as nitration enhances WT α-Syn propensity to aggregate (Hodara et al. (2004) J. Biol. Chem., 279:47746-47753; Uversky et al. (2001) J. Biol. Chem., 276:10737-10744; Uversky et al. (2005) Brain Res. Mol. Brain Res., 134:84-102; Yamin et al. (2003) FEBS Lett., 542:147-152). Oxidized and aggregated α-Syn, when released from dying neurons, may stimulate scavenger receptors on microglia resulting in their sustained activation and dopaminergic neurodegeneration (Wersinger et al. (2006) Curr. Med. Chem., 13: 591-602; Zhang et al. (2005) FASEB J., 19:533-542; Croisier et al. (2005) J. Neuroinflammation 2:14). Moreover, activated microglia generate nitric oxide and superoxide that rapidly react to form peroxynitrite which can then traverse cell membranes resulting in 3-nitrotyrosine (NT) formation, DNA damage, mitochondrial inhibition, or lipid peroxidation (Dringen, R. (2005) Antioxid. Redox. Signal 7:1223-1233; Ischiropoulos, et al. (2003) J. Clin. Invest., 111:163-169). Despite these understandings, compositions and methods for the treatment of neurological diseases such as Parkinson's disease are needed.

SUMMARY OF THE INVENTION

In accordance with the instant invention methods of inhibiting, treating, and/or preventing a central nervous system disease or disorder in a patient in need thereof are provided. In a particular embodiment, the central nervous system disease or disorder is characterized by the presence of nitrated alpha-synuclein and/or Lewy bodies. In a particular embodiment, the central nervous system disease or disorder is Parkinson's disease. The methods of the instant invention comprise administering to a subject: a) a nitrated alpha synuclein peptide, and b) an adjuvant that stimulates regulatory T cells.

In accordance with another aspect of the instant invention, compositions comprising the nitrated alpha synuclein peptide are provided. In a particular embodiment, the composition further comprises an adjuvant that stimulates regulatory T cells and/or at least one pharmaceutically acceptable carrier.

BRIEF DESCRIPTION OF THE DRAWINGS

FIG. 2 provides the amino acid sequence of human alpha-synuclein (SEQ ID NO: 8).

DETAILED DESCRIPTION OF THE INVENTION

Figure 1:
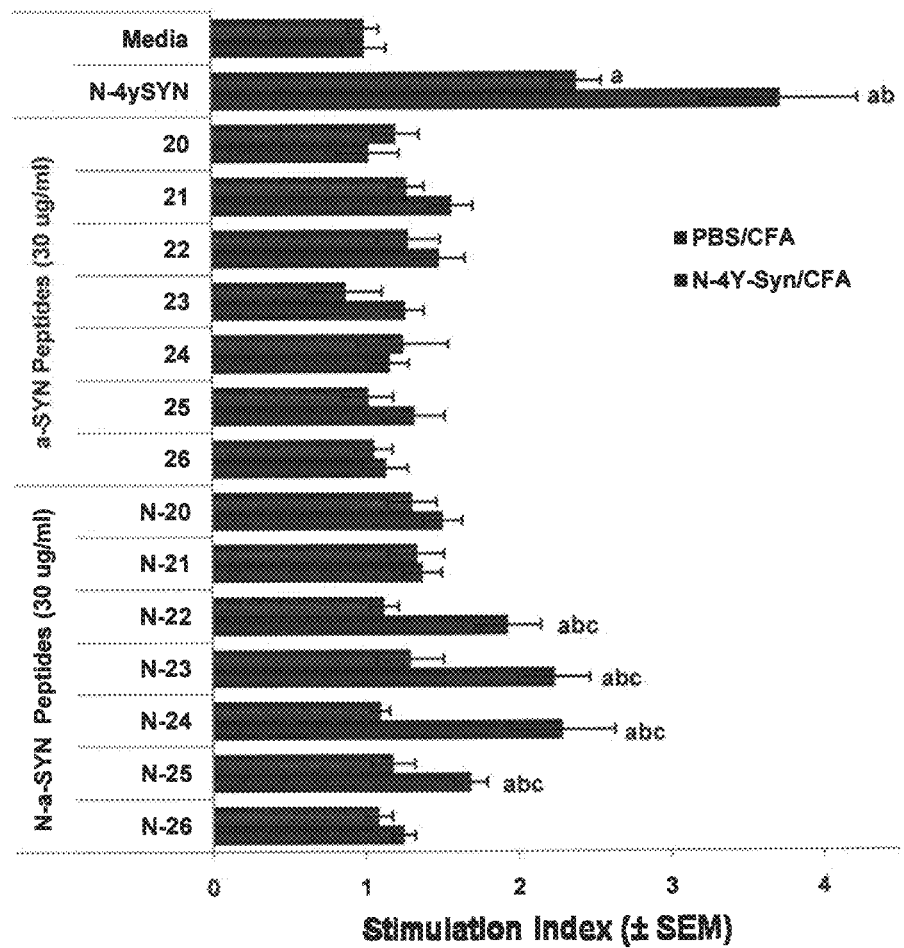
FIG. 1 provides the results of a lymphocyte proliferation assessment of donor splencoytes cultured in the presence of media alone or media containing 30 µg/ml of antigen (N-4YSyn, non-niteated peptides (a-SYN perptides), or nitrated peptides (N-a-SYN peptides) for 5 days and using standard $^3$H-thymidine incorporation assays. Top bars represent splenocytes from mice immunized with phosphate buffered saline (PBS) in complete Freund's adjuvant (CFA) and bottom bars represent splenocytes from mice immunized with N-4YSyn in complete Freund's adjuvant (CFA). P<0.05 compared to $^a$ media control; $^b$ PBS/CFA immune; $^c$ non-nitrated peptide.

The neuropathology of Parkinson's disease (PD) includes loss of dopaminergic neurons in the substantia nigra, nitrated alpha-synuclein (N-alpha-Syn) enriched intraneuronal inclusions or Lewy bodies and neuroinflammation. While the contribution of innate microglial inflammatory activities to disease are known, evidence for how adaptive immune mechanisms may affect the course of PD remains obscure. Microglia neuroinflammatory responses speed neurodegenerative events. This can be slowed by adoptive transfer of T cells from Copolymer-1-immunized mice administered to 1-methyl-4-phenyl-1,2,3,6-tetrahydropyridine (MPTP) recipients. The cellular basis for this neuroprotective response was the CD4+ T cell population, suggesting involvement of CD4+CD25+ regulatory T cells (Tregs), cells known to suppress immune activation and maintain immune homeostasis and tolerance. Adoptive transfer of CD3-activated Tregs to MPTP-intoxicated mice provides greater than 90% protection of the nigrostriatal system (Reynolds et al., J. Leuk. Biol. (2007) 82:1083-1094). The response was dose-dependent and paralleled modulation of microglial responses and up-regulation of glial cell-derived neurotrophic factor (CDNF) and TGF-beta. Interestingly, that adoptive transfer of effector T cells showed no significant neuroprotective activities. Tregs were found to mediate neuroprotection through suppression of microglial responses to stimuli, including aggregated, nitrated alpha-synuclein. Moreover, Treg-mediated suppression was also operative following removal of Tregs from culture prior to stimulation. This neuroprotection was achieved through modulation of microglial oxidative stress and inflammation. As Tregs can be modulated in vivo, these data demonstrate the ability to use of such immunomodulatory strategies to treat PD.

PD-associated oxidative protein modifications can create novel antigenic epitopes capable of peripheral adaptive T cell responses that can affect nigrostriatal degeneration. Nitrotyrosine (NT)-modified alpha-synuclein can be detected readily in cervical lymph nodes (CLN) from MPTP intoxicated mice. Antigen-presenting cells within the CLN show increased surface expression of major histocompatibility complex class II, initiating the molecular machinery necessary for efficient antigen presentation. MPTP-treated mice also produce antibodies to native and nitrated alpha-Syn. Further, mice immunized with the NT-modified C-terminal tail fragment of alpha-Syn, but not native protein, generate robust T cell proliferative and pro-inflammatory secretory responses specific only for the modified antigen (Benner et al., PLoS One (2008) 3:e1376). Notably, T cells generated against the nitrated epitope do not respond to the unmodified protein. Mice deficient in T and B lymphocytes are also resistant to MPTP-induced neurodegeneration while the transfer of T cells from mice immunized with N-alpha-synuclein leads to a robust neuroinflammatory response with accelerated dopaminergic cell loss. These data show that NT modifications within alpha-synuclein can bypass or break immunological tolerance and activate peripheral leukocytes in draining lymphoid tissue. Thus, NT modifications in alpha-synuclein induce adaptive immune responses that exacerbate PD pathobiology.

The neuroimmune degenerative activities associated with PD, in significant measure, are Th17 cell-mediated, with CD4(+)CD25(+) regulatory T cell (Treg) dysfunction seen among populations of N-alpha-synuclein induced T cells. Purified vasoactive intestinal peptide induced and natural Tregs reverse the N-alpha-synuclein T cell nigrostriatal degeneration (Reynolds et al., J. Immunol. (2010) 184: 2261-71). Indeed, combinations of adoptively transferred N-alpha-synuclein and vasoactive intestinal peptide immunocytes or natural Tregs administered to MPTP mice attenuate microglial inflammatory responses and lead to robust nigrostriatal protection. These results demonstrate Treg control of N-alpha-synuclein induce neurodestructive immunity.

In accordance with the instant invention, methods of inhibiting, treating, and/or preventing a central nervous system disease or disorder are provided. In a preferred embodiment, the central nervous system disease or disorder is characterized by the presence of aggregated and/or nitrated alpha-synuclein and/or Lewy bodies. In a particular embodiment, the central nervous system disease is Parkinson's disease. In a particular embodiment, the methods comprise administering to a subject in need thereof a therapeutically effective amount of: 1) at least one nitrated alpha-synuclein peptide of the instant invention and 2) at least one adjuvant that stimulates functional regulatory T cells. The immunogen and adjuvant may be contained in the same composition or be present in separate compositions. The composition(s) may comprise at least one pharmaceutically acceptable carrier. When the compositions are administered separately, the compositions may be administered simultaneously or sequentially. For example, the adjuvant may be administered first and then the nitrated alpha-synuclein peptide; the nitrated alpha-synuclein peptide may be administered first and then the adjuvant; or multiple administrations of each component may be used in any order.

In a particular embodiment, the methods of the instant invention prevent a central nervous system disease or disorder. In a particular embodiment, the methods of the instant invention delay or inhibit the onset of the central nervous system disease or disorder and/or symptoms associated therewith. For example, the compositions of the instant invention may be administered to a healthy individual, particularly one at risk for a central nervous disease or disorder. The compositions of the instant invention may be administered as a vaccine.

The methods of the instant invention may further comprise administering other therapies which are beneficial to the treatment of the particular central nervous system disease or disorder. In a particular embodiment, the methods of the instant invention further comprise administering full length, nitrated alpha-synuclein and/or another fragment thereof (see, e.g., the fragments of U.S. patent application Ser. No. 12/500,414). The methods of the instant invention may also further comprise the step of monitoring the subject for the central nervous system disease or disorder after the administration of the compositions of the instant invention. For example, the subject may be monitored at least once, at least twice, at least three times or more after treatment. The monitoring may be performed over the course of weeks, months, and/or years. The central nervous system disease or disorder may be monitored through, for example, biological (clinical) diagnosis and/or monitoring of the symptoms associated with the central nervous system disease or disorder.

In accordance with another aspect of the instant invention, compositions comprising at least one nitrated alpha-synuclein peptide are provided. The compositions may be used for the treatment/inhibition/prevention of a central nervous system disease or disorder. In one embodiment, the composition comprises at least one nitrated alpha-synuclein peptide of the instant invention and at least one pharmaceutically acceptable carrier. The composition may further comprise at least one adjuvant that stimulates the production of regulatory T cells. The above compositions may further comprise further comprise administering full length, nitrated alpha-synuclein and/or another fragment thereof. In a particular embodiment, the instant invention encompasses a kit comprising at least two compositions: wherein one composition comprises the nitrated alpha-synuclein peptide and, optionally, at least one pharmaceutically acceptable carrier; and the second composition comprises the adjuvant and, optionally, at least one pharmaceutically acceptable carrier.

In a particular embodiment, the central nervous disease or disorder of the instant invention is a central nervous system disease or disorder characterized by the presence of aggregated and/or nitrated alpha-synuclein. In a particular embodiment, the central nervous system disease or disorder is characterized by the presence of Lewy bodies. In a particular embodiment, the central nervous system disease or disorder is a synucleinopathy. Examples of central nervous system diseases and disorders include, without limitation, dementia (e.g., dementia with Lewy bodies), multiple system atrophy, pure autonomic failure, neurodegeration with barin iron accumulation, Parkinson's Disease, and Alzheimer's disease (Yashimoto (1995) PNAS 92:9141).

In a particular embodiment, the adjuvant induces a T cell phenotypic switch from pro-inflammatory (TH1 and TH17) to anti-inflammatory and regulatory (TH2, Treg, and Tr1). In other words, the adjuvants are compounds capable of activating regulatory T cells. In a particular embodiment, the adjuvant of the instant invention is selected from the group consisting of histone deacetylase (HDAC) inhibitors (e.g., trichostatin-A (TSA)), anti-CD3 antibodies (e.g., otelixizumab), glatiramer acetate (Cop-1, Copaxone®), neuropeptides such as vasoactive intestinal peptide (VIP) and VIP analogs (see, e.g., U.S. Patent Application Publication No. 2011/0178017), vitamin D (1 alpha, 25-dihydroxyvitamin D3), retinoic acid, interlekin-2 (IL-2) optionally with glucocorticoid (e.g., dexamethasone), granulocyte macrophages colony stimulating factor (GM-CSF), glucocorticoid-induced tumor necrosis factor receptor (GITR) ligand (e.g., Fc-GITR-L (a fusion protein comprising an Fc fragment and the GITRL extracellular domain)), anti-tumor necrosis factor alpha (TNF-α) antibodies (e.g., infliximab), venom immunotherapy (e.g., hymenoptera venom immunotherapy), and transforming growth factor beta (TGFβ). In a particular embodiment, the adjuvant is vasoactive intestinal peptide (particularly human, but the instant invention encompasses VIP from other species and analogs thereof). In a particular embodiment, the adjuvant is GM-CSF.

In a particular embodiment, the immune response (e.g., humoral immune response) induced by the administration of a composition of the instant invention to a subject causes the abnormal protein (nitrated alpha synuclein) which characterizes the central nervous disease or disorder to be substantially reduced (preferably eliminated) from the site of abnormal expression (e.g., within the central nervous system).

The nitrated alpha synuclein peptide of the instant invention may be a fragment of an alpha synuclein from any species, particularly human. In a particular embodiment, the peptide is about 10 to about 35 amino acids, about 10 to about 30 amino acids, about 10 to about 25 amino acids, about 10 amino acids to about 20 amino acids, about 12 to about 18 amino acids, about 14 to about 16 amino acids, or about 15 amino acids. In a particular embodiment, the fragment is from the C-terminal 40 amino acids of alpha synuclein (e.g., amino acids 101-140 of SEQ ID NO: 8). In a particular embodiment, the fragment is derived from amino acids corresponding to 106-135 of SEQ ID NO: 8, particularly amino acids 106-130 of SEQ ID NO: 8. As stated hereinabove, the alpha synuclein peptide/fragment is nitrated. The fragment may comprise at least one, at least two, at least three, at least four, at least five or more of the tyrosines nitrated into nitrotyrosines (e.g., tyrosines at positions 125, 133, and/or 136). In a particular embodiment, the fragment comprises only one tyrosine or nitrotyrosine. Peptides (e.g., tyrosines in the peptides) may be nitrated by methods known in the art. For example, peptides may be nitrated in the presence of peroxynitrite, tetranitromethane, nitric oxide, nitrogen dioxide, nitrous acid, nitryl chloride, acyl nitrates, alkyl nitrates, or metal nitrates (Abello et al. (2009) J. Proteome Res., 8:3222) In a particular embodiment, the fragment comprises the nitrotyrosine corresponding to position Y125 of SEQ ID NO: 8. The peptide may optionally have an N-terminal methionine added.

The nitrated alpha synuclein peptides of the instant invention may have 75%, 80%, 85%, 90%, 95%, 97%, or 99% homology/identity with any of the alpha synuclein sequences provided herein (e.g., any one of SEQ ID NOs: 1-13). In a particular embodiment, the nitrated alpha synuclein peptides of the instant invention may have 75%, 80%, 85%, 90%, 95%, 97%, or 99% homology/identity with SEQ ID NO: 3, SEQ ID NO: 4, SEQ ID NO: 5, or SEQ ID NO: 6. The nitrated alpha synuclein peptides of the instant invention may vary from the recited SEQ ID NOs by addition, deletion, and/or substitution.

In a particular embodiment, the nitrated alpha synuclein peptide has at least 75%, 80%, 85%, 90%, 95%, 97%, 99%, or 100% homology with:

```
                                            (SEQ ID NO: 9)
          GAPQEGILEDMPVDPDNEAYEMPSE.
```

The nitrated alpha synuclein peptide may comprise SEQ ID NO: 9 plus 1, 2, 3, 4, or 5 amino acids at the N- and/or C-terminus, which may be selected to correspond with the full-length alpha synuclein (e.g., SEQ ID NO: 8).

In a particular embodiment, the nitrated alpha synuclein peptide has at least 75%, 80%, 85%, 90%, 95%, 97%, 99%, or 100% homology with:

```
                                            (SEQ ID NO: 3)
          GYPQEGILEDMPVDP
          or
                                            (SEQ ID NO: 10)
          GAPQEGILEDMPVDP.
```

The nitrated alpha synuclein peptide may comprise SEQ ID NO: 3 or 10 plus 1, 2, 3, 4, or 5 amino acids at the N- and/or C-terminus, which may be selected to correspond with the full-length alpha synuclein (e.g., SEQ ID NO: 8).

In a particular embodiment, the nitrated alpha synuclein peptide has at least 75%, 80%, 85%, 90%, 95%, 97%, 99%, or 100% homology with:

```
                                            (SEQ ID NO: 4)
          GILEDMPVDPGSEAY
          or
                                            (SEQ ID NO: 11)
          GILEDMPVDPDNEAY.
```

The nitrated alpha synuclein peptide may comprise SEQ ID NO: 4 or 11 plus 1, 2, 3, 4, or 5 amino acids at the N- and/or C-terminus, which may be selected to correspond with the full-length alpha synuclein (e.g., SEQ ID NO: 8).

In a particular embodiment, the nitrated alpha synuclein peptide has at least 75%, 80%, 85%, 90%, 95%, 97%, 99%, or 100% homology with:

```
                                            (SEQ ID NO: 5)
          MPVDPGSEAYEMPSE
          or
                                            (SEQ ID NO: 12)
          MPVDPDNEAYEMPSE.
```

The nitrated alpha synuclein peptide may comprise SEQ ID NO: 5 or 12 plus 1, 2, 3, 4, or 5 amino acids at the N- and/or C-terminus, which may be selected to correspond with the full-length alpha synuclein (e.g., SEQ ID NO: 8).

In a particular embodiment, the nitrated alpha synuclein peptide has at least 75%, 80%, 85%, 90%, 95%, 97%, 99%, or 100% homology with:

```
                                          (SEQ ID NO: 6)
GSEAYEMPSEEGYQD
or
                                          (SEQ ID NO: 13)
DNEAYEMPSEEGYQD.
```

The nitrated alpha synuclein peptide may comprise SEQ ID NO: 6 or 13 plus 1, 2, 3, 4, or 5 amino acids at the N- and/or C-terminus, which may be selected to correspond with the full-length alpha synuclein (e.g., SEQ ID NO: 8).

The peptides of the present invention may be prepared in a variety of ways, according to known methods. The peptides may be purified from appropriate sources, e.g., transformed bacterial or animal cultured cells or tissues, by a variety of purification methods including, for example, immunoaffinity purification. The availability of nucleic acid molecules encoding the alpha-synuclein peptide enables production of the peptides using in vitro expression methods and cell-free expression systems known in the art. In vitro transcription and translation systems are commercially available, e.g., from Promega Biotech (Madison, WI) or Gibco-BRL (Gaithersburg, MD).

Larger quantities of alpha-synuclein peptides may be produced by expression in a suitable prokaryotic or eukaryotic system. For example, part or all of a DNA molecule encoding for alpha-synuclein may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

Alpha-synuclein peptides produced by gene expression in a recombinant prokaryotic or eukaryotic system may be purified according to methods known in the art. A commercially available expression/secretion system can be used, whereby the recombinant peptide is expressed and thereafter secreted from the host cell, and readily purified from the surrounding medium. If expression/secretion vectors are not used, an alternative approach involves purifying the recombinant peptide by affinity separation, such as by immunological interaction with antibodies that bind specifically to the recombinant peptide or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

Alpha-synuclein peptides of the invention, prepared by the aforementioned methods, may be analyzed according to standard procedures. For example, such peptides may be subjected to amino acid sequence analysis, according to known methods.

As stated hereinabove, the alpha-synuclein peptides of the instant invention may contain substitutions within any of the alpha synuclein sequences described herein (e.g., any one of SEQ ID NOs: 1-13). These substitutions may be conservative (e.g., an acidic amino acid in place of another acidic amino acid, a basic amino acid in place of a basic amino acid, a large hydrophobic amino acid in place of a large hydrophobic, etc.). The substitutions may comprise amino acid analogs and mimetics.

The alpha-synuclein peptides of the instant invention may have capping, protecting and/or stabilizing moieties at the C-terminus and/or N-terminus. Such moieties are well known in the art and include, without limitation, amidation and acetylation. The peptide template may also be lipidated or glycosylated at any amino acid (i.e., a glycopeptide). The alpha-synuclein peptides of the instant invention may also comprise at least one D-amino acid instead of the native L-amino acid. In a particular embodiment, the peptides may comprise only D-amino acids. In a particular embodiment, the peptide is phosphorylated at Sen 29. This phosphorylation promotes aggregation, toxicity, and immunogenicity (Braithwaite et al. (2012) Rev. Neurosci., 23:191; Chen et al. (2005) Nat. Neurosci., 8:657).

The peptides of the instant invention may also be linked/conjugated to a carrier protein/peptide, particularly one that increases the immunogenicity of the alpha-synuclein peptide. Carrier proteins are preferably proteins that are non-toxic and non-reactogenic and obtainable in sufficient amount and purity. Examples of carrier proteins include, without limitation, non-toxic/inactivated bacterial toxins (toxoid; e.g., diphtheria toxoid (e.g., CRM197), tetanus toxoid, pertussis toxoid, cholera toxoid, *E. coli* LT, *E. coli* ST, and exotoxin A from *Pseudomonas aeruginosa*), albumin, ovalbumin, keyhole limpet hemocyanin (KLH), bovine serum albumin (BSA), and C5a or fragments thereof (see, e.g., PCT/US96/16825). In a particular embodiment, alpha-synuclein peptide is linked to C5A or a fragment thereof.

Nucleic acid molecules encoding the peptides of the invention may be prepared by any method known in the art such as (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acid sequences encoding the peptides of the invention may be isolated from appropriate biological sources using methods known in the art. In one embodiment, a cDNA clone of alpha-synuclein is isolated (e.g., from a cDNA expression library, particularly of human origin) and modified to create the alpha-synuclein peptides of the instant invention. In an alternative embodiment, utilizing the sequence information provided by the cDNA sequence, genomic clones encoding alpha-synuclein may be isolated.

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Alpha-synuclein peptide encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the alpha-synuclein peptide nucleic acid molecules of the invention. Primers capable of specifically amplifying alpha-synuclein peptide encoding nucleic acids described herein are also contemplated herein. Such oligonucleotides are useful as probes and primers for detecting, isolating or amplifying alpha-synuclein peptide encoding nucleic acids.

It will be appreciated by persons skilled in the art that variants (e.g., allelic variants) of alpha-synuclein sequences exist, for example, in the human population, and may be taken into account when designing and/or utilizing oligonucleotides of the invention. Accordingly, it is within the scope of the present invention to encompass such variants, with respect to the alpha-synuclein peptide sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Such variants would not demonstrate substantially altered alpha-synuclein activity or protein levels.

The present invention also encompasses pharmaceutical compositions comprising at least one alpha-synuclein peptide in a pharmaceutically acceptable carrier. Such a pharmaceutical composition may be administered, in a therapeutically effective amount, particularly with an adjuvant that stimulates functional regulatory T cells, to a patient in need thereof. The pharmaceutical compositions of the present invention can be administered by any suitable route, for example, by injection, by oral, pulmonary, nasal, topical, or other modes of administration such as controlled release devices. In a particular embodiment, the composition is delivered by injection. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins) which are herein incorporated by reference. The pharmaceutical composition of the present invention can be prepared, for example, in liquid form, or can be in dried powder form (e.g., lyophilized).

The compositions described herein will generally be administered to a patient as a pharmaceutical preparation. The term "patient" or "subject", as used herein, refers to human or animal subjects. The compositions of the instant invention may be employed therapeutically, under the guidance of a physician.

The compositions of the instant invention may be conveniently formulated for administration with any pharmaceutically acceptable carrier(s). For example, the active agents may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the active agents in the chosen medium may be varied and the medium may be chosen based on the desired route of administration of the pharmaceutical preparation. Except insofar as any conventional media or agent is incompatible with the active agents to be administered, its use in the pharmaceutical preparation is contemplated.

The dose and dosage regimen of the compositions according to the invention that are suitable for administration to a particular patient may be determined by a physician considering the patient's age, sex, weight, general medical condition, and the specific condition for which the active agent is being administered and the severity thereof. The physician may also take into account the route of administration, the pharmaceutical carrier, and the particular agent's biological activity.

Selection of a suitable pharmaceutical preparation will also depend upon the mode of administration chosen. For example, the compositions of the invention may be administered by direct injection to a desired site. In this instance, a pharmaceutical preparation comprises the active agents of the instant invention dispersed in a medium that is compatible with the site of injection. The compositions of the instant invention may be administered by any method. For example, the compositions can be administered, without limitation parenterally, subcutaneously, orally, topically, pulmonarily, rectally, vaginally, ocularly, intravenously, intraperitoneally, intracranial, intrathecally, intracerbrally, epidurally, intramuscularly, intradermally, or intracarotidly. In a particular embodiment, the compositions are administered intravenously, subcutaneously, or orally or by direct injection. Pharmaceutical preparations for injection are known in the art. If injection is selected as a method for administering the compositions, steps must be taken to ensure that sufficient amounts of the molecules reach their target cells to exert a biological effect. Dosage forms for parenteral administration include, without limitation, solutions, emulsions, suspensions, dispersions and powders/granules for reconstitution.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of the composition may be determined by evaluating the toxicity of the molecules or cells in animal models. Various concentrations of active agents in pharmaceutical preparations may be administered to mice or other animal models, and the minimal and maximal dosages may be determined based on the beneficial results and side effects observed as a result of the treatment. Appropriate dosage unit may also be determined by assessing the efficacy of the treatment in combination with other standard drugs. The dosage units of the compositions of the instant invention may be determined individually or in combination with each treatment according to the effect detected.

The pharmaceutical preparation of the instant invention may be administered at appropriate intervals (e.g., at least one booster), for example, once every 2-4 days, once a week, or once every 2-6 of weeks until the pathological symptoms are reduced or alleviated, after which the dosage may be reduced to a maintenance level or eliminated. The appropriate interval in a particular case would normally depend on the condition of the patient. In a particular embodiment, the composition is administered to the body in an isotonic solution at physiological pH 7.4. However, the complexes can be prepared before administration at a pH below or above pH 7.4.

Definitions

The following definitions are provided to facilitate an understanding of the present invention:

The singular forms "a," "an," and "the" include plural referents unless the context clearly dictates otherwise.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a central nervous disease or disorder herein may refer to curing, relieving, and/or preventing the central nervous system disease or disorder, a symptom(s) of it, or the predisposition towards it.

As used herein, the term "subject" refers to an animal, particularly a mammal, particularly a human.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, Polysorbate 80), emulsifier, buffer (e.g., Tris HCl, acetate, phosphate), bulking substance (e.g., lactose, mannitol), excipient, auxilliary agent, filler, disintegrant, lubricating agent, binder, stabilizer, preservative or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers. An isolated compound may be substantially pure.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% or more by weight of the given compound. Purity is measured by methods appropriate for the given compound (e.g. chromatographic methods, agarose or polyacrylamide gel electrophoresis, HPLC analysis, and the like).

An "immunogen" refers to a compound comprising a peptide, polypeptide or protein which is "immunogenic," i.e., capable of eliciting, augmenting or boosting an immune response (e.g., cellular and/or humoral). The immunogen can be recombinantly produced. An immunogen comprises at least one antigenic determinant or epitope.

As used herein, "regulatory T cells" are CD4+CD25+ cells that exhibit immuno-inhibitory properties.

A "carrier protein" refers to a polypeptide that can be coupled with a polypeptide or a peptide of the invention to form a coupled protein. A carrier protein may be coupled to a polypeptide or peptide in order to increase the immunogenicity of the polypeptide or peptide.

The following example is provided to illustrate certain embodiments of the invention. It is not intended to limit the invention in any way.

EXAMPLE

Animals

Male 6-7 week old, C57BL/6J (stock 000664, denoted as B6) (H-$2^b$) mice were purchased from Jackson Laboratories (Bar Harbor, ME). All animal procedures were in accordance with National Institutes of Health (NIH) guidelines and approved by the Institutional Animal Care and Use Committee (IACUC) of the University of Nebraska Medical Center (UNMC).

Immunization and Immune Cell Adoptive Transfers

B6 (H-$2^b$) mice were immunized with PBS or 50 µg of N-4YSyn (nitrated C-terminal 40 amino acid α-Syn fragment) in complete Freund's adjuvant (CFA) administered subcutaneously (s.c.). Seven days after primary immunization, mice were boosted with another 50 μg of antigen emulsified in IFA (Sigma-Aldrich). Seven days following their final immunizations, donor mice were sacrificed and single cell suspensions were prepared from the spleen.
$^3$H-Thymidine In Vitro Proliferation/Sensitivation Assays Samples of pooled splenocytes were tested for their proliferative capacity by $^3$H-thymidine incorporation after stimulation with either immunizing antigen or test peptide. Splenocytes were plated at a density of 2×10$^6$ cells/ml complete RPMI tissue culture media (RPMI 1640 supplemented with 10% fetal bovine serum (FBS), 2 mM L-glutamine, 10 mM HEPES, 1 mM sodium pyruvate, 1× non-essential aa, 55 μM 2-mercaptoethanol, 100 U/ml penicillin, and 100 μg/ml streptomycin (Mediatech Inc., Herndon, VA)). Splenocytes from PBS or N-4YSyn immunized mice were stimulated with 0 or 30 μg/ml of immunizing antigen N-4YSyn or 30 μg/ml of the non-nitrated or nitrated peptide indicated, and cultured at 37° C. for 5 days. Cells were pulsed with 1 mCi $^3$H-thymidine/well for the final 18 hours of culture, harvested onto glass fiber plates, and counted by β-scintillation spectrometry (TopCount, Packard-PerkinElmer Instruments, Wellesley, MA).

Results

To test immune responses to particular epitopes within N-α-Syn, mice were immunized with N-4YSyn or PBS emulsified in complete Freund's adjuvant (CFA). Seven days following the initial immunization, mice were boosted with their respective immunogens emulsified in incomplete Freund's adjuvant (IFA). Seven days later, mice were sacrificed and splenocytes were tested for antigen-specific T cell proliferative responses to N-4YSyn or peptide epitope (nitrated or non-nitrated; Table 1). Stimulation with N-4YSyn yielded a significant proliferative response from splenocytes of mice immunized with N-4YSyn and challenged in vitro with N-4YSyn, but not media control. Moreover, stimulation with nitrated peptides 22, 23, 24, and 25, but not non-nitrated peptides, yielded a significant proliferative response from splenocytes of mice immunized with N-4YSyn, but not control (PBS) immunized mice (FIG. 1). These data demonstrate the immune reactivity of the nitrated tyrosines at position 107 and 125 of α-synuclein.

TABLE 1

Amnio acid sequences of peptides with amino acid positions within murine α-synuclein.

| Peptide (SEQ ID NO) | Sequence | Start | End |
| --- | --- | --- | --- |
| 20 (1) | KKDQMGKGEEGYPQE | 96 | 110 |
| 21 (2) | GKGEEGYPQEGILED | 101 | 115 |
| 22 (3) | GYPQEGILEDMPVDP | 106 | 120 |
| 23 (4) | GILEDMPVDPGSEAY | 111 | 125 |
| 24 (5) | MPVDPGSEAYEMPSE | 116 | 130 |
| 25 (6) | GSEAYEMPSEEGYQD | 121 | 135 |
| 26 (7) | EMPSEEGYQDYEPEA | 126 | 140 |

Tyrosines are blooded and underlined and may be nitrated.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising: a) an alpha-synuclein peptide, wherein said alpha-synuclein peptide consists of SEQ ID NO: 11, wherein said alpha-synuclein peptide is amidated or acetylated, and wherein said alpha-synuclein peptide comprises at least one nitrotyrosine; and b) a pharmaceutically acceptable carrier.

2. A composition comprising: a) an alpha-synuclein peptide, wherein said alpha-synuclein peptide consists of SEQ ID NO: 3, wherein said alpha-synuclein peptide is amidated or acetylated, and wherein said alpha-synuclein peptide comprises at least one nitrotyrosine; and b) a pharmaceutically acceptable carrier.

* * * * *